United States Patent [19]

Matsumoto et al.

[11] Patent Number: 5,795,774
[45] Date of Patent: Aug. 18, 1998

[54] BIOSENSOR

[75] Inventors: Toru Matsumoto; Masako Furusawa; Narushi Ito; Shinya Nakamoto, all of Tokyo, Japan

[73] Assignee: NEC Corporation, Tokyo, Japan

[21] Appl. No.: 891,197

[22] Filed: Jul. 10, 1997

[30] Foreign Application Priority Data

Jul. 10, 1996 [JP] Japan .................................. 8-180286

[51] Int. Cl.⁶ .......................... C12M 3/00; G01N 27/36
[52] U.S. Cl. .................... 435/287.9; 204/403; 204/415; 204/418
[58] Field of Search ................... 435/287.9; 204/400, 204/403, 415, 416, 418

[56] References Cited

U.S. PATENT DOCUMENTS 5,110,441  5/1992  Kinlen et al. .................. 204/418
5,466,575  11/1995  Cozzette et al. ................ 435/6

FOREIGN PATENT DOCUMENTS

| 63-304150 | 12/1988 | Japan . |
| 7-159366 | 6/1995 | Japan . |
| 8-16669 | 2/1996 | Japan . |
| 8-50112 | 2/1996 | Japan . |

*Primary Examiner*—David A. Redding
*Attorney, Agent, or Firm*—Sughrue, Mion, Zinn, Macpeak & Seas, PLLC

[57] ABSTRACT

A drop in measurement accuracy of biosensors, due to interferents in a measurement sample is avoided by an arrangement wherein: a hydrogen peroxide electrode 2 is formed on an insulated base 1, and then a γ-aminopropyltriethoxysilane film 3, an acetylcellulose film 4, a perfluorocarbonsulfonic acid resin film 5, an organic macromolecular film 6 incorporating an immobilized enzyme with catalytic properties, and a polyalkylsiloxane film 7, are sequentially formed on the electrode 2.

9 Claims, 7 Drawing Sheets

POLYALKYLSILOXANE CONCENTRATIONS (%):

- ■ 7.0(%)
- ◇ 8.8
- * 10.5
- □ 12.3
- ◆ 14.0

BIOSENSOR

BACKGROUND OF THE INVENTION

1. Field of the Invention

The present invention relates to a biosensor for analysing a specific constituent within a sample using electrochemical methods, and in particular relates to a biosensor which allows measurement over a wide concentration range, which is unaffected by obstructing or interfering substances such as oxidation-reduction material, and which enables suppression of any reduction in the accuracy of the measurement due to the pH value of the sample being measured.

2. Description of the Related Art

The measurement accuracy of biosensors in which a specific constituent of a measurement sample is converted to hydrogen peroxide by the catalytic effect of an enzyme, and an electrochemical reaction of the hydrogen peroxide is then used to measure the concentration of the specific constituent, are affected greatly by material within the sample being measured, which causes oxidation-reduction reactions other than that of hydrogen peroxide (this type of material herein referred to as an interferent), at the electrode surface of the sensor. This effect is a particular problem in the measurement of bodily fluids such as urine and blood. Examples of interferents include ascorbic acid, uric acid and acetaminophen. Amperometric measuring methods for preventing the effect of these interferents involve covering the electrode surface with a fluorine ion exchange macromolecular film or a film of a cellulose derivative, thus restricting the permeation of any interferents through to the electrode surface.

For example, in Japanese Patent Application, First Publication No. Hei-7-159366, acetylcellulose and ion exchange films were used for restricting the permeation of interferents through to the electrode surface of a portable measuring device. The configuration used in the above patent application for restricting the permeation of interferents through to the electrode surface is shown in FIG. 12. In FIG. 12, numeral 20 refers to a sensor holder inside of which is incorporated an enzyme sensor 38. A backing electrode 30 comprising a planar hydrogen peroxide electrode, is formed by selectively forming a thin film metal electrode 32 of a metal such as platinum, gold or silver on the surface of a ceramic or resin film 31. Numeral 33 refers to an immobilized enzyme film which is fixed on to the backing electrode. Typical examples of the immobilized enzyme film 33 include sandwich configurations where an immobilized enzyme layer comprising an enzyme such as glucose oxidase or lactic acid oxidase, is protected by an upper and a lower layer. An immobilized enzyme layer 35 is formed by methods such as cross linking using a cross linking agent, or by entrapment methods where the enzyme is coated with a gel lattice or a macromolecule. A lower protective film 34 restricts the permeation of interferents through to the surface of the electrode, and must display good adhesiveness and stability with respect to the backing electrode 30 and the immobilized enzyme layer 35, and consequently, acetylcellulose or ion exchange films are often used. An upper protective film 36 protects the immobilized enzyme layer 35 and restricts the diffusion of the substrate towards the immobilized enzyme layer 35, and must display good adhesiveness with respect to the immobilized enzyme layer as well as good mechanical strength. A surface protection film 37 of a material such a nylon lattice or a polycarbonate is adhered separately to the upper surface of the upper protective film 36 to strengthen the functionality of the upper protective film 36. The various layers are produced using dip coat methods or spin coat methods, enabling the production of thin, uniform films. For example, the lower protective film 34 is formed by dripping a 5% acetylcellulose film solution (in a 3:1 acetone:cyclohexane solvent mixture) onto the metal electrode 32 and then rotating the electrode at 2000 rpm for a period of 5 seconds. The immobilized enzyme layer 35 is formed using the same spin coat method used to produce the lower protective film 34, but using an enzyme solution formed by mixing the enzyme with a 0.5% solution of glutaraldehyde which has been treated with a 0.1M phosphate buffer solution (pH 7.0). The upper protective film 36 is formed by dip coating in a 2.5% acetylcellulose film solution (in a 1:1 acetone:ethanol solvent mixture) at a rate of 1 cm/second.

The following techniques are known for restricting the excess diffusion of a material to be measured towards an organic macromolecular film containing an immobilized enzyme with catalytic properties. For example, in the technique reported in Japanese Patent Application, First Publication No. Sho-63-304150, a sandwich configuration in which glucose oxidase was immobilized between two films was employed. The outer film comprised a polycarbonate which restricted the penetration of macromolecules such as proteins, and the diffusion of glucose. This film increased the range of concentrations which the sensor could be used to measure. The inner film comprised silicone rubber, methyl methacrylate or acetylcellulose which allowed only hydrogen peroxide to penetrate, thus inhibiting the permeation of interferents. In order to achieve the best levels of hydrogen peroxide permeability and strength, acetylcellulose of 2-3 μm was found to be preferable.

Furthermore, in the technique reported in Japanese Patent Application, Second Publication No. Hei-8-16669, a film of which the major component was silicone was used as the film for restricting the permeation of glucose. An example of the technique reported in this patent application is shown in FIG. 13. A working electrode 10, a counter electrode 11, and a reference electrode 12 are formed on an insulated base 1. Next, a film of immobilized glucose oxidase 41 and a film of silicone 42 are formed using photolithography methods, and finally the entire arrangement is cut into chips to make glucose sensors. In the manufacturing method for glucose sensors outlined in this invention, because the film patterning is completed using photolithography methods, the production of large volumes of glucose sensors with the same properties is possible.

As reported in Japanese Patent Application, First Publication No. Hei-8-50112, another technique currently employed for increasing the measurement accuracy employs a Nafion film to eliminate any change over time in the sensor response, after the response has reached a peak level. An example of the technique reported in this patent is shown in FIG. 14. A working electrode 10, a counter electrode 11, and a reference electrode 12 are formed on an insulated base 1. The working electrode 10 is covered sequentially with a film of acetylcellulose 51, a film 52 comprising a mixture of glucose oxidase and photo cross linked polyvinyl alcohol, and a film of Nafion 53, forming a sandwich configuration glucose biosensor. Furthermore, the region surrounding the working electrode 10 is insulated with silicone adhesive 54. In the glucose biosensors of this invention, the film of acetylcellulose 51 is positioned on the working electrode side of the film 52 comprising a mixture of glucose oxidase and photo cross linked polyvinyl alcohol, thus preventing the permeation of interferents such as ascorbic acid, and allowing only hydrogen peroxide to be transmitted. Furthermore the skeletal film of Nafion 53 is positioned on the opposite side of the film 52, thus eliminating any change over time in the response value after the response has reached a peak level, and improving the response properties of the sensor.

The following problems occur in the amperometic measuring techniques outlined above. A first problem is that the restriction of the permeation of interferents through to the electrode surface is insufficient. The reason for this is that in order to ensure sufficient restriction of the permeation of interferents with just a single permeation restriction film, either the thickness of the permeation restriction film must be increased, or alternatively the concentration of the primary constituents in the permeation restriction layer must be increased. However so doing causes a restriction in the transmission of hydrogen peroxide, resulting in a loss in the response speed and the response output of the biosensor.

A second problem is that when the material to be measured is present in the sample at high concentration levels, current permeation restriction films are unable to sufficiently restrict the diffusion of the material to be measured, and the sensor output becomes saturated. The reason for this is that because large amounts of the material to be measured diffuse into the organic macromolecular film, the enzyme immobilized within the organic macromolecular film is unable to convert all the material to be measured to hydrogen peroxide.

A third problem is that the sensor output fluctuates with the pH of the measurement sample. The reason for this is that the enzyme immobilized within the organic macromolecular film has an associated optimum pH level, and so the activity of the enzyme will be affected by fluctuations in the measurement sample pH, thus generating fluctuations in the sensor output.

SUMMARY OF THE INVENTION

An object of the present invention is to provide a biosensor incorporating a permeation restriction film or films which adequately restrict the permeation of interferents through to the electrode.

Another object of the present invention is to provide a biosensor in which the output does not become saturated, even when the concentration of the material to be measured in the sample is high.

Yet another object of the present invention is to provide a biosensor in which the output fluctuates very little, even when the measurement sample pH fluctuates.

A first biosensor of the present invention comprises a configuration in which a γ-aminopropyltriethoxysilane film, an acetylcellulose film, a perfluorocarbonsulfonic acid resin film, and then an organic macromolecular film incorporating an immobilized enzyme with catalytic properties, are sequentially formed on top of an electrode which has been formed on top of an insulated base.

The γ-aminopropyltriethoxysilane film and the acetylcellulose film, a derivative of cellulose, have permeation restriction properties in that they are both dense layers which incorporate minute apertures which exclude molecules with high molecular weights, while the perfluorocarbonsulfonic acid resin film, an ion exchange film based around a perfluorocarbon skeleton, has permeation restriction properties in that it excludes atoms or molecules which are charged. Consequently, there is an increase in permeation restriction properties with respect to high concentrations of interferents beyond that observed for any one of the three films. Furthermore, because the perfluorocarbonsulfonic acid resin film formed on top of the acetylcellulose film does not inhibit the transmission of the uncharged hydrogen peroxide through to the hydrogen peroxide electrode, there is no reduction in the detectability of hydrogen peroxide.

A second biosensor of the present invention comprises a configuration in which a γ-aminopropyltriethoxysilane film, an acetylcellulose film, a perfluorocarbonsulfonic acid resin film, an organic macromolecular film with catalytic properties, and then a film in which the major constituent is polyalkylsiloxane, are sequentially formed on top of an electrode which has been formed on top of an insulated base.

By layering a film in which the major constituent is polyalkylsiloxane on top of the organic macromolecular film incorporating an immobilized enzyme with catalytic properties, the permeation of macromolecules such as proteins, and the diffusion of the material to be measured can be restricted, making it possible to stabilize the sensor output from the biosensor as well as expand the concentration range over which the biosensor can be used. Furthermore, it reduces the effect of the measurement sample pH on the sensor output.

The biosensors of the present invention are able to achieve the following effects.

A first effect is that measurements of a specific constituent within a sample which contains high concentrations of interferents can be conducted with good levels of accuracy. The reason for this is that because the hydrogen peroxide electrode is sequentially covered by a film of γ-aminopropyltriethoxysilane, a film of acetylcellulose and a film of perfluorocarbonsulfonic acid resin, the restriction on the transmission of hydrogen peroxide produced within the organic macromolecular film incorporating an enzyme with catalytic properties, through to the electrode is suppressed to a minimum level, while the permeation of interferents through to the electrode is adequately restricted.

A second effect is that measurements of a specific constituent within a sample can be conducted with good levels of accuracy for an expanded range of concentrations, and even for samples with a large variation in pH level. The reason for this is that by forming a film of polyalkylsiloxane on top of the organic macromolecular film incorporating an immobilized enzyme with catalytic properties, excess diffusion of the material to be measured is restricted.

A third effect is that production of the biosensors can be completed in large quantities and at low cost. The reason for this is that the majority of currently employed processes for semiconductor production can be applied to this invention.

A fourth effect is that the actual measuring device itself can be miniaturized. The reason for this is that a counter electrode and a reference electrode can be formed together with the active electrode on the same insulated base.

A fifth effect is that a plurality of different constituents within a sample can be measured concurrently. The reason for this is that films of γ-aminopropyltriethoxysilane, acetylcellulose, and perfluorocarbonsulfonic acid resin can be formed over the top of a plurality of active electrodes, and then separate films of organic macromolecules incorporating different immobilized enzymes can be formed above each of the working electrodes.

DESCRIPTION OF THE PREFERRED EMBODIMENTS

Figure 1:
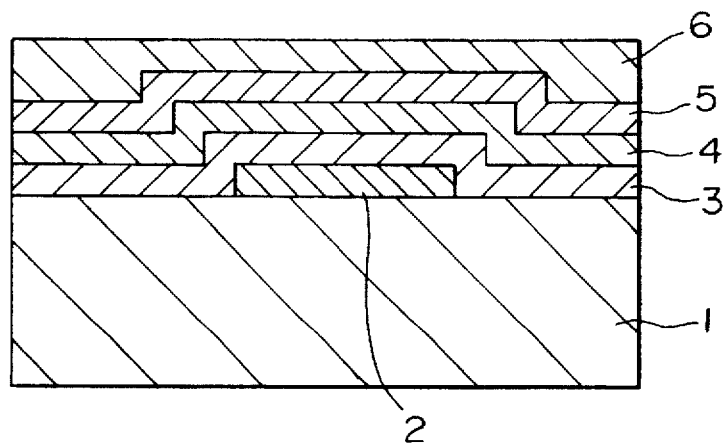
FIG. 1 is a cross-sectional diagram of a first embodiment of a biosensor of the present invention.

Next is a description of a first embodiment of the present invention with reference to the drawings. A cross-sectional composition diagram of a biosensor of the first embodiment of the present invention is shown in FIG. 1. The configuration of this biosensor comprises a hydrogen peroxide electrode 2 formed on an insulated base 1, and then a first film 3 of γ-aminopropyltriethoxysilane, a second film 4 of acetylcellulose, a third film 5 of perfluorocarbonsulfonic acid resin, and then a fourth film 6 comprising an organic macromolecular film with catalytic properties, sequentially formed on top of the electrode 2. The insulated base 1 can be made of any highly insulating material in which ceramics, glass, or quartz are the major constituent, but it must display excellent water resistant, heat resistant and chemical resistant properties and display excellent adhesiveness with respect to the electrode 2. The hydrogen peroxide electrode 2 can be any material in which platinum, gold or silver is the major constituent, although platinum, which will not react with the sample and which displays excellent chemical resistant properties and excellent hydrogen peroxide detection characteristics is preferable. Furthermore, a platinum electrode can be formed on top of the insulated base 1 by sputtering, ion plating, vacuum deposition, chemical vapor deposition, or electrolytic methods, although sputtering methods which enable low cost formation of a platinum film on the insulated base 1 in a relatively short time are preferable.

Figure 5:
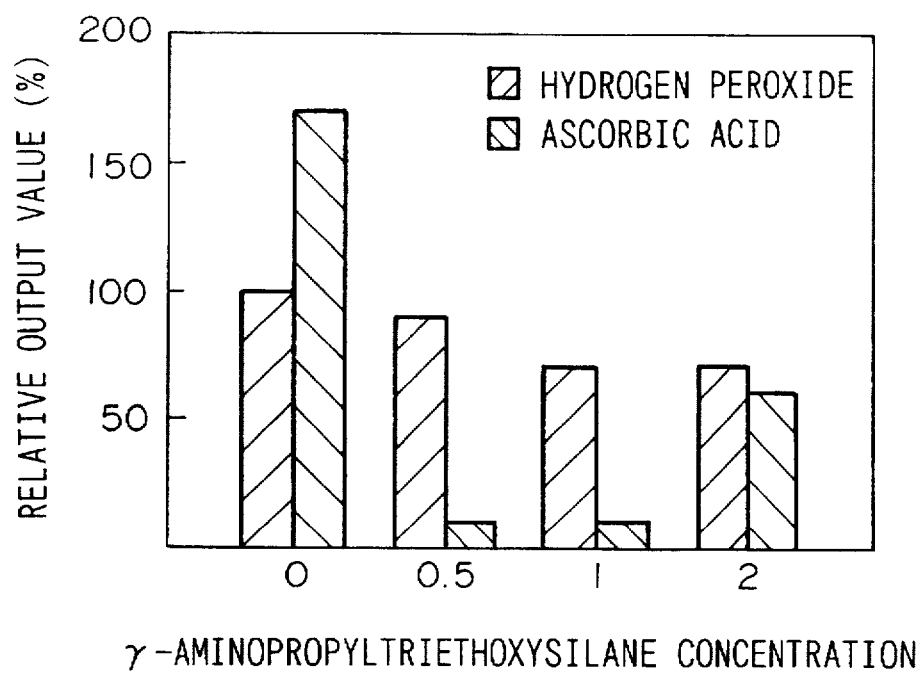
FIG. 5 is a graph showing a relationship between γ-aminopropyltriethoxysilane concentration and relative output.

The γ-aminopropyltriethoxysilane film 3 which is the first film formed on top of the hydrogen peroxide electrode 2 is formed by dripping a solution of γ-aminopropyltriethoxysilane diluted with pure water, onto the hydrogen peroxide electrode 2 and then using spin coating methods. The reason for diluting the γ-aminopropyltriethoxysilane with pure water is that dilution with pure water causes the alkoxyl groups of the γ-aminopropyltriethoxysilane to hydrolyze, thus producing silanol groups. Concentrations of 0.5~2 (v/v %) of γ-aminopropyltriethoxysilane dissolved in pure water are preferable. This is because, as is shown in FIG. 5, when solutions of 0, 0.5, 1.0, 2.0 (v/v %) γ-aminopropyltriethoxysilane in pure water were dripped onto separate hydrogen peroxide electrodes, and films of γ-aminopropyltriethoxysilane produced by spin coating methods, and then the current output values at each electrode with respect to hydrogen peroxide and ascorbic acid displayed as relative output values, it was observed that selective permeation restriction of only the interferents (ascorbic acid) was displayed for γ-aminopropyltriethoxysilane concentrations of 0.5~2 (v/v %). It is even more desirable to use a γ-aminopropyltriethoxysilane concentration of 1 (v/v %), as this is the concentration at which the most marked improvement in permeation restriction properties was observed.

Figure 6:
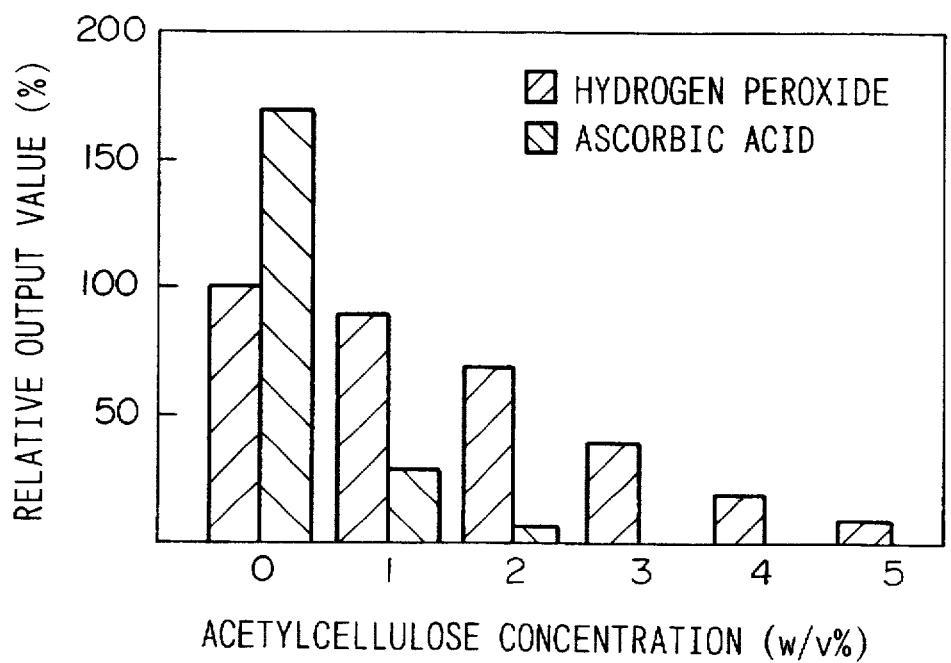
FIG. 6 is a graph showing a relationship between acetylcellulose concentration and relative output.

Next, the acetylcellulose film 4 is formed by dissolving acetylcellulose in acetone, dripping the solution onto the γ-aminopropyltriethoxysilane film 3 and then using spin coating methods. The reason for using an acetone solution is that because acetylcellulose displays a high solubility in acetone, it is easy to solubilize. An acetylcellulose concentration of 0.5~5 (w/w %) in acetone is preferable. This is because, as shown in FIG. 6, when solutions of 0, 1, 2, 3, 4, 5 (w/v %) acetylcellulose in acetone were dripped onto separate γ-aminopropyltriethoxysilane films and then films of acetylcellulose produced by spin coating methods, and then the current output values at each electrode with respect to hydrogen peroxide and ascorbic acid displayed as relative output values, and the ratio of the hydrogen peroxide current output value with respect to the acetylcellulose concentration and the ascorbic acid output value with respect to the acetylcellulose concentration calculated as relative output values, it was observed that selective permeation restriction of only the interferents (ascorbic acid) was displayed for acetylcellulose concentrations of 0.5~5 (w/v %). Furthermore, it was even more desirable to use an acetylcellulose concentration of 2 w/v %, as this is the concentration at which the most marked improvement in permeation restriction properties was observed.

Figure 7:
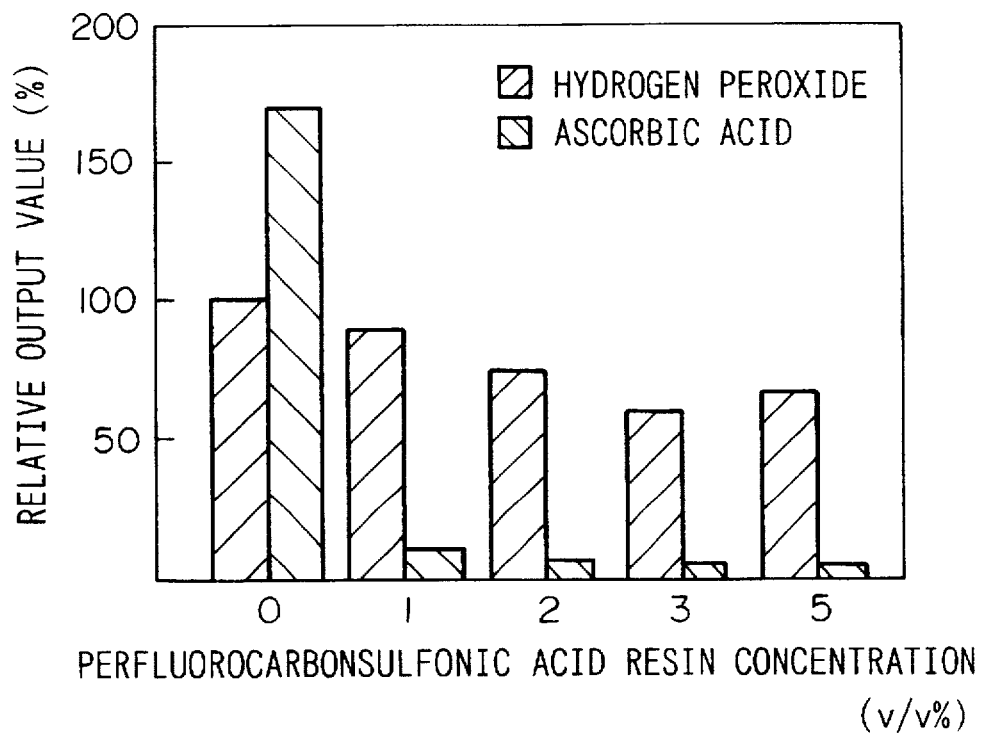
FIG. 7 is a graph showing a relationship between perfluorocarbonsulfonic acid resin concentration and relative output.

Next, the perfluorocarbonsulfonic acid resin film 5 is formed by dissolving perfluorocarbonsulfonic acid resin in ethanol, dripping the solution onto the acetylcellulose film 4 and then using spin coating methods. The ethanol solvent can be replaced by isopropyl alcohol but the cheaper ethanol is preferable. Perfluorocarbonsulfonic acid resin concentrations of 1 (v/v %) or greater are preferable. This is because, as is shown in FIG. 7, when solutions of 0, 1, 2, 3, 5 (w/v %) perfluorocarbonsulfonic acid resin in ethanol were dripped onto separate acetylcellulose films, and films of perfluorocarbonsulfonic acid resin formed by spin coating methods, and then the current output values at each electrode with respect to hydrogen peroxide and ascorbic acid displayed as relative output values, it was observed that permeation restriction of the interferents (ascorbic acid) was displayed for perfluorocarbonsulfonic acid resin concentrations of 1~5 (v/v %). It is even more desirable to use a perfluorocarbonsulfonic acid resin concentration of 5 (v/v %), as this is the concentration at which the most marked improvement in permeation restriction properties was observed.

Next, the organic macromolecular film 6 incorporating an immobilized enzyme with catalytic properties is formed by dripping a water solution containing 0.1~2% (v/v %) of glutaraldehyde, albumin onto the perfluorocarbonsulfonic acid resin film 5 and then using spin coating methods.

Figure 8:
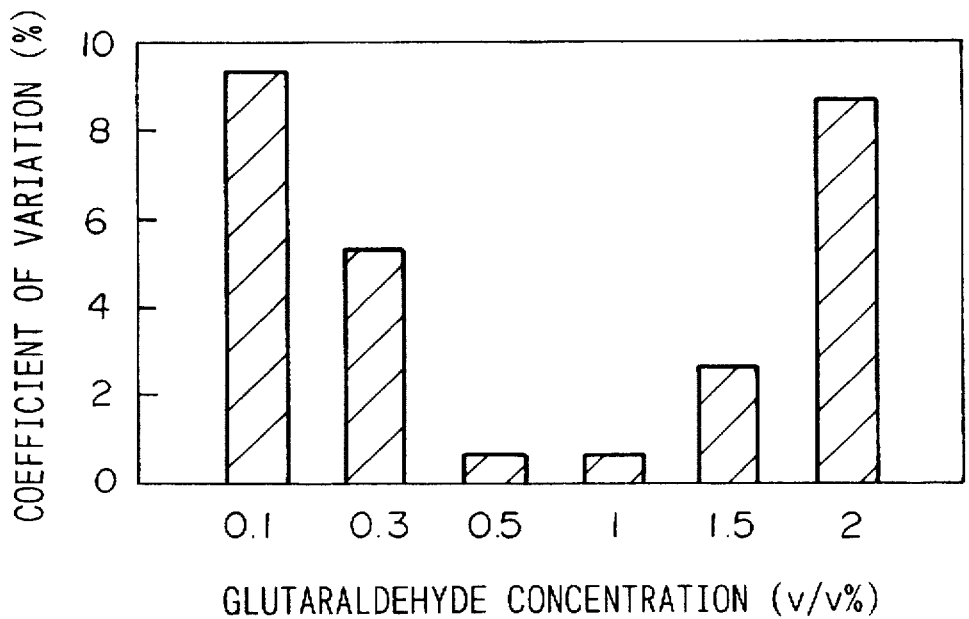
FIG. 8 is a graph showing a relationship between glutaraldehyde concentration and coefficient of variation.

Examples of the various enzymes which will produce hydrogen peroxide as a result of the catalysis include lactate oxidase, glucose oxidase, urea se, uric acid oxidase, galactose oxidase, lactose oxidase, sucrose oxidase, ethanol oxidase, methanol oxidase, starch oxidase, amino acid oxidase, monoamine oxidase, cholesterol oxidase, choline oxidase, and pyruvic acid oxidase. As is shown in FIG. 8, preferable concentrations of glutaraldehyde in the water solution range from 0.1–2 (v/v %), with concentrations of 0.5–1 (v/v %) being even more desirable. This is because concentrations within this range enable the production of biosensors with stabilized output.

Regarding the method used for forming the films, any method which yields a film of uniform thickness is suitable, and so other methods such as spray coating can also be used in place of the spin coating method.

Figure 2:
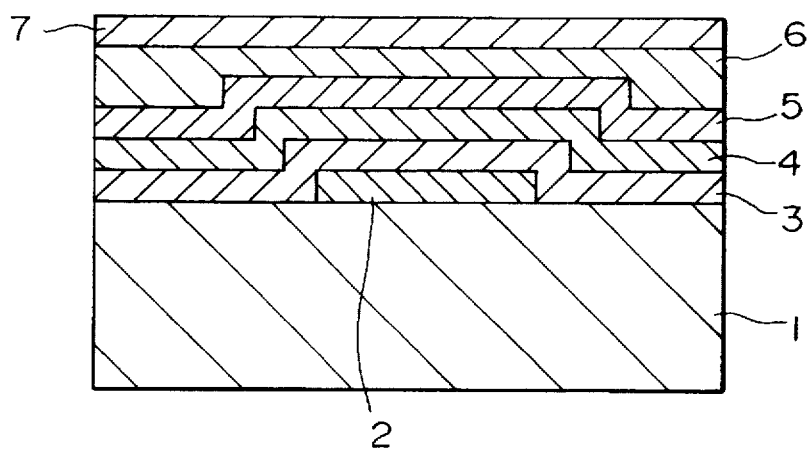
FIG. 2 is a cross-sectional diagram of a second embodiment of a biosensor of the present invention.

Next is a description of a second embodiment of the present invention with reference to the drawings. A cross-sectional diagram of the second embodiment is shown in FIG. 2. The configuration of this biosensor comprises a hydrogen peroxide electrode 2 positioned on top of an insulated base 1, and then a first film 3 of γ-aminopropyltriethoxysilane, a second film 4 of acetylcellulose, a third film 5 of perfluorocarbonsulfonic acid resin, a fourth film 6 comprising an organic macromolecular film with catalytic properties, and then a fifth film 7 of polyalkylsiloxane, sequentially formed on top of the electrode 2.

The hydrogen peroxide electrode 2, and the γ-aminopropyltriethoxysilane film 3, the acetylcellulose film 4, the perfluorocarbonsulfonic acid resin film 5, and the organic macromolecular film 6 incorporating an immobilized enzyme with catalytic properties, are formed sequentially by the same methods outlined in the first embodiment. Next, the polyalkylsiloxane film 7 is formed by dripping a solution containing 7% (v/v %) or greater concentration of polyalkylsiloxane onto the organic macromolecular film 6 with catalytic properties, and using spin coating methods. The reason for employing polyalkylsiloxane concentrations of 7 (v/v %) or greater is to ensure adequate permeation restriction properties in the polyalkylsiloxane film, and in order to ensure even better permeation restriction properties, concentrations of 10 (v/v %) or greater are preferable.

Figure 3:
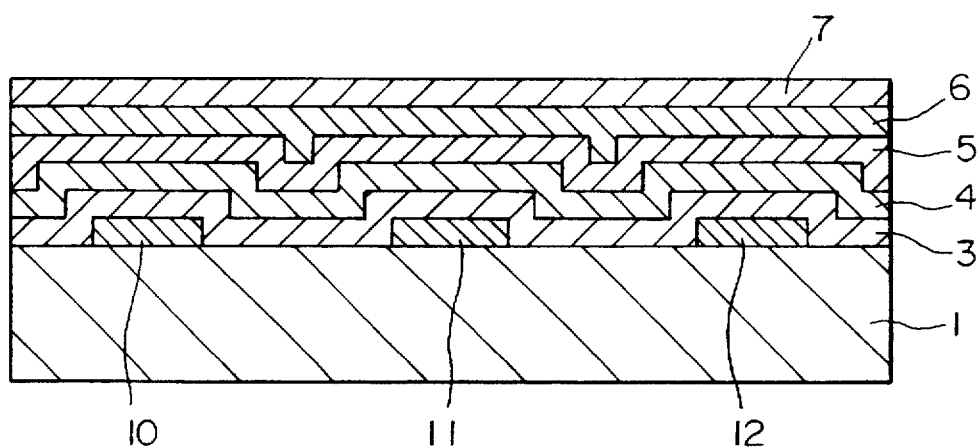
FIG. 3 is a cross-sectional diagram of a third embodiment of a biosensor of the present invention.

Next is a detailed description of a third embodiment of the present invention with reference to FIG. 3. This figure shows a cross-sectional diagram of the third embodiment which comprises a working electrode 10, a counter electrode 11, and a reference electrode 12 positioned on top of an insulated base 1, and then a γ-aminopropyltriethoxysilane film 3, an acetylcellulose film 4, a perfluorocarbonsulfonic acid resin film 5, and an organic macromolecular film 6 with catalytic properties, sequentially formed on top of the electrodes. The working electrode 10 can be made of platinum, gold or carbon, although the use of platinum, which displays excellent hydrogen peroxide detection characteristics, and which is also highly acid resistant and chemical resistant is desirable.

Furthermore, formation of the working electrode 10 on the insulated base 1 is best achieved by sputtering methods which enable low cost formation of a platinum film in a relatively short time. The counter electrode 11 can be made of platinum, silver or carbon, although the use of platinum, which displays excellent conductivity, and which is also highly acid resistant and chemical resistant is desirable. Furthermore, formation of the counter electrode 11 on the insulated base 1 is best achieved by sputtering methods which enable low cost formation of a platinum film in a relatively short time. The reference electrode 12 is made of silver/silver chloride. The silver/silver chloride electrode can be best formed by first using the sputtering methods mentioned above to form a silver film, and then using either electrolytic polymerization in a hydrochloric acid solution, or immersion of the silver film in a solution containing either a metal chloride with a greater ionization tendency than silver or a metal chloride with a low oxidation reduction potential, to form the silver chloride. These methods offer the lowest cost and the greatest ease of manufacture, and are thus most suitable for large volume production.

Using the same methods outlined in the first embodiment, a γ-aminopropyltriethoxysilane film 3, an acetylcellulose film 4, a perfluorocarbonsulfonic acid resin film 5, and an organic macromolecular film 6 with catalytic properties, are formed on top of these electrodes. Furthermore, it is also possible to form a polyalkyl siloxane film 7 on top of the organic macromolecular film 6 with catalytic properties, using the same method outlined in the second embodiment.

In addition to offering the same effects as the first and second embodiments, this embodiment also enables the miniaturization of the measuring device in which the biosensor is mounted, a simplification of the measuring device, and furthermore a reduction in manufacturing costs, because the working electrode, the counter electrode and the reference electrode are all located on a single insulated base.

Figure 4:
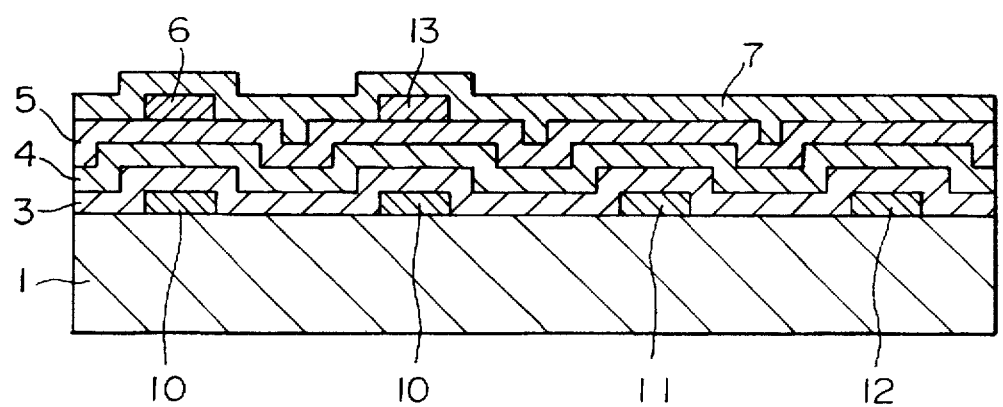
FIG. 4 is a cross-sectional diagram of a fourth embodiment of a biosensor of the present invention.

Next is a detailed description of a fourth embodiment of the present invention with reference to FIG. 4. This figure shows a cross-sectional diagram of the fourth embodiment which comprises two active electrodes 10 positioned on top of an insulated base 1, and then a γ-aminopropyltriethoxysilane film 3, an acetylcellulose film 4, and a perfluorocarbonsulfonic acid resin film 5 sequentially formed on top of the electrodes, as was described in the first embodiment. An organic macromolecular film 6 with catalytic properties, and another organic macromolecular film 13 with catalytic properties are then formed so that one of the two films 6, 13 sits above each of the two working electrodes 10 respectively. The formation of the organic macromolecular film 6 incorporating an immobilized enzyme with catalytic properties, and the different organic macromolecular film 13 incorporating an immobilized enzyme with catalytic properties, is achieved by photolithography. The organic macromolecular film 6 with catalytic properties, and the different organic macromolecular film 13 with catalytic properties could be for example an organic macromolecular film incorporating immobilized lactate oxidase and an organic macromolecular film incorporating immobilized glucose oxidase respectively. There is no limit on the number of working electrodes and organic macromolecular films with catalytic properties which can be formed on the insulated base 1. Moreover, it is also possible to form a polyalkylsiloxane film 7 over the top of the organic macromolecular films with catalytic properties, in the same manner as in the second embodiment.

Using this embodiment it is possible to produce a biosensor which is capable of analysing two different constituents within a sample concurrently. Furthermore, because there is no limit on the number of working electrodes 10 and organic macromolecular films with catalytic properties, it is also possible to produce biosensors which are capable of analysing three or more specific constituents.

Below are descriptions of some examples of the present invention

EXAMPLE 1

A first glucose sensor was formed on top of a hydrogen peroxide electrode having an electrode surface area of 3 mm² formed on top of an insulated base, by using spin coat methods to sequentially produce films from a 1 (v/v %) water solution of γ-aminopropyltriethoxysilane, and then from an albumin solution containing glucose oxidase and 0.55 (v/v %) of glutaraldehyde. A second glucose sensor was formed on top of another hydrogen peroxide electrode of the same type, by using spin coat methods to sequentially produce films from a 1 (v/v %) water solution of γ-aminopropyltriethoxysilane, a 2 (w/v %) solution of acetylcellulose, and then from an albumin solution containing glucose oxidase and 0.5 (v/v %) of glutaraldehyde. A third glucose sensor was formed on top of yet another hydrogen peroxide electrode of the same type, by using spin coat methods to sequentially produce films from a 1 (v/v %) water solution of γ-aminopropyltriethoxysilane, a 2 (w/v %) solution of acetylcellulose, a 5 (v/v %) solution of perfluorocarbonsulfonic acid resin, and then from an albumin solution containing glucose oxidase and 0.5 (v/v %) of glutaraldehyde.

Evaluation of the glucose sensors was conducted by measuring the glucose concentration in a 100 (mg/dl) glucose solution containing 40 (mg/dl) of ascorbic acid as an interferent and then comparing the measurements. Table 1 shows the output values for each of the different film configurations expressed as a relative percentage value, with the measured value obtained for a 100 (mg/dl) glucose solution containing no interferents deemed to be 100%. Hence, the closer the relative percentage listed in Table 1 is to 100%, the lower the effect is of interferents on that particular film configuration.

As the results show, the glucose sensor formed by using spin coat methods to sequentially produce films from a 1 (v/v %) solution of γ-aminopropyltriethoxysilane, a 2 (w/v %) solution of acetylcellulose, a 5 (v/v %) solution of perfluorocarbonsulfonic acid resin, and then from an albumin solution containing glucose oxidase and 0.5 (v/v %) of glutaraldehyde is totally unaffected by the interferent, and was thus able to accurately measure the glucose concentration.

TABLE 1

(Evaluation of the effect of interferents on glucose sensors formed with differing film configurations)

| Film configuration | Relative output value (%) |
| --- | --- |
| APTES* | 322 |
| APTES + acetylcellulose | 186 |
| APTES + acetylcellulose + perfluorocarbonsulfonic acid resin | 100 |

*γ-aminopropyltriethoxysilane

EXAMPLE 2

A first glucose sensor was formed on top of a hydrogen peroxide electrode having an electrode surface area of 3 mm² formed on top of an insulated base, by using spin coat methods to produce films from a 1 (v/v %) water solution of γ-aminopropyltriethoxysilane, and then from an albumin solution containing glucose oxidase and 0.5 (v/v %) of glutaraldehyde. A second glucose sensor was formed on top of another hydrogen peroxide electrode of the same type, by using spin coat methods to sequentially produce films from a 1 (v/v %) water solution of γ-aminopropyltriethoxysilane, a 2 (w/v %) solution of acetylcellulose, and then from an albumin solution containing glucose oxidase and 0.5 (v/v %) of glutaraldehyde. A third glucose sensor was formed on top of yet another hydrogen peroxide electrode of the same type, by using spin coat methods to sequentially produce films from a 1 (v/v %) water solution of γ-aminopropyltriethoxysilane, a 2 (w/v %) solution of acetylcellulose, a 5 (v/v %) solution of perfluorocarbonsulfonic acid resin, and then from an albumin solution containing glucose oxidase and 0.5 (v/v %) of glutaraldehyde.

Evaluation of the glucose sensors was conducted by measuring and comparing the time taken for the current output values to reach a stable reading during measurement of a 100 (mg/dl) glucose solution. The results are shown in Table 2. As the results show, glucose sensors produced using the materials described above, with the configurations outlined above, have no effect on the time required for a stable reading. This suggests that the materials and the configurations described above are not affecting the enzyme matrix.

TABLE 2

(Evaluation of the effect of interferents on glucose sensors formed with differing film configurations)

| Film configuration | Measurement time (seconds) |
| --- | --- |
| APTES | 30 |
| APTES + acetylcellulose | 29 |
| APTES + acetylcellulose + perfluorocarbonsulfonic acid resin | 31 |

EXAMPLE 3

Three different glucose sensors were formed on top of three separate hydrogen peroxide electrodes, each of which was formed on top of an insulated base having an electrode surface area of 3 mm², by using spin coat methods to first produce films from 0.5, 1, and 2 (v/v %) water solutions of γ-aminopropyltriethoxysilane respectively on top of the three electrodes, and then sequentially covering each configuration with films produced by spin coating a 2 (w/v %) solution of acetylcellulose, a 5 (v/v %) solution of perfluorocarbonsulfonic acid resin, and an albumin solution containing glucose oxidase and 0.5 (v/v %) of glutaraldehyde.

Evaluation of the glucose sensors was conducted by measuring the glucose concentration in a 100 (mg/dl) glucose solution containing 40 (mg/dl) of ascorbic acid as an interferent and then comparing the measurements. Table 3 shows the output values for each of the different film configurations expressed as a relative percentage value, with the measured value obtained for a 100 (mg/dl) glucose solution containing no interferents deemed to be 100%. Hence, the closer the relative percentage listed in Table 3 is to 100%, the lower the effect is of interferents on that particular film configuration. The results show that an γ-aminopropyltriethoxysilane concentration of 1 (v/v %) is optimum.

TABLE 3

(Evaluation of the effect of interferents on glucose sensors formed with differing film configurations, produced by altering the γ-aminopropyltriethoxysilane concentration)

| γ-aminopropyltriethoxysilane concentration (v/v%) | Relative output value (%) |
| --- | --- |
| 0.5 | 183 |
| 1 | 100 |
| 2 | 136 |

EXAMPLE 4

Five different glucose sensors were formed on top of five separate hydrogen peroxide electrodes, each of which was formed on top of an insulated base having an electrode surface area of 3 mm², by using spin coat methods to produce a film from a 1 (v/v %) water solution of γ-aminopropyltriethoxysilane on each electrode, covering these films with films produced by spin coating 1, 2, 3, 4 and 5 (w/v %) solutions of acetylcellulose respectively, and then sequentially covering each configuration with films produced by spin coating a 5 (v/v %) solution of perfluorocarbonsulfonic acid resin, and an albumin solution containing glucose oxidase and 0.5 (v/v %) of glutaraldehyde.

Evaluation of the glucose sensors was conducted by measuring the glucose concentration in a 100 (mg/dl) glucose solution containing 40 (mg/dl) of ascorbic acid as an interferent and then comparing the measurements. Table 4 shows the output values for each of the different film configurations expressed as a relative percentage value, with the measured value obtained for a 100 (mg/dl) glucose solution containing no interferents deemed to be 100%. Hence, the closer the relative percentage listed in Table 4 is to 100%, the lower the effect is of interferents on that particular film configuration. As the results show, the optimum acetylcellulose concentration for reducing the effect of interferents is 2 (w/v %).

TABLE 4

(Evaluation of the effect of interferents on glucose sensors formed with differing film configurations, produced by altering the acetylcellulose concentration)

| Acetylcellulose concentration (w/v %) | Relative output value (%) |
| --- | --- |
| 1 | 225 |
| 2 | 100 |
| 3 | 95 |
| 4 | 87 |
| 5 | 71 |

EXAMPLE 5

Three different glucose sensors were formed on top of three separate hydrogen peroxide electrodes, each of which was formed on top of an insulated base having an electrode surface area of 3 mm², by using spin coat methods to sequentially produce films from a 1 (v/v %) water solution of γ-aminopropyltriethoxysilane and a 2 (w/v %) solution of acetylcellulose on top of each electrode, covering these films with films produced by spin coating 1, 2 and 5 (v/v %) solutions of perfluorocarbonsulfonic acid resin respectively, and then covering each of the configurations with an albumin solution containing glucose oxidase and 0.5 (v/v %) of glutaraldehyde.

Evaluation of the glucose sensors was conducted by measuring the glucose concentration in a 100 (mg/dl) glucose solution containing 40 (mg/dl) of ascorbic acid as an interferent and then comparing the measurements. Table 5 shows the output values for each of the different film configurations expressed as a relative percentage value, with the measured value obtained for a 100 (mg/dl) glucose solution containing no interferents deemed to be 100%. Hence, the closer the relative percentage listed in Table 5 is to 100%, the lower the effect is of interferents on that particular film configuration. As the results show, the optimum perfluorocarbonsulfonic acid resin concentration for reducing the effect of interferents is 5 (v/v %).

TABLE 5

(Evaluation of the effect of interferents on glucose sensors formed with differing film configurations, produced by altering the perfluorocarbonsulfonic acid concentration)

| Perfluorocarbonsulfonic acid concentration (w/v %) | Relative output value (%) |
| --- | --- |
| 1 | 196 |
| 2 | 132 |
| 5 | 100 |

EXAMPLE 6

Three different ethanol sensors were formed on top of three separate hydrogen peroxide electrodes, each of which was formed on top of an insulated base having an electrode surface area of 3mm². One ethanol sensor was formed by using spin coat methods to produce films from a 1 (v/v %) water solution of γ-aminopropyltriethoxysilane, a 2 (w/v %) solution of acetylcellulose, a 5 (v/v %) solution of perfluorocarbonsulfonic acid resin, and then from an albumin solution containing glucose oxidase and 0.5 (v/v %) of glutaraldehyde. A second ethanol sensor was formed on another electrode using the same methods to produce films from a 1 (v/v %) water solution of γ-aminopropyltriethoxysilane, a 2 (w/v %) solution of acetylcellulose, a 5 (v/v %) solution of perfluorocarbonsulfonic acid resin, and then from an albumin solution containing lactate oxidase and 0.5 (v/v %) of glutaraldehyde. A third ethanol sensor was formed on yet another electrode using the same methods to produce films from a 1 (v/v %) water solution of γ-aminopropyltriethoxysilane, a 2 (w/v %) solution of acetylcellulose, a 5 (v/v %) solution of perfluorocarbonsulfonic acid resin, and then from an albumin solution containing ethanol oxidase and 0.5 (v/v %) of glutaraldehyde.

Evaluation of the ethanol sensors was conducted by measuring the respective concentrations in a 100 (mg/dl) glucose solution, a 200 µM lactate solution and a 0.1 (w/v %) ethanol solution, each of which contained 40 (mg/dl) of ascorbic acid as an interferent, and then comparing the measurements. Table 6 shows the output values for each of the different film configurations expressed as a relative percentage value, with the measured values obtained for a 100 (mg/dl) glucose solution, a 200 µM lactate solution and a 0. 1 (w/v %) ethanol solution, each containing no interferents, deemed to be 100%. Hence, the closer the relative percentage listed in Table 6 is to 100%, the lower the effect is of interferents on that particular film configuration. As the results show, for biosensors produced using the materials described above, with the configurations outlined above, the effect of interferents is greatly reduced regardless of which oxidase is used for detection purposes.

TABLE 6

(Evaluation of the effect of interferents on the measurement of specific constituents in a solution, using biosensors produced from a variety of different oxidases)

| Oxidase used | Relative output value (%) |
| --- | --- |
| Glucose oxidase | 100 |
| Lactate oxidase | 101 |
| Ethanol oxidase | 99 |

EXAMPLE 7

A glucose sensor was formed on top of a hydrogen peroxide electrode having an electrode surface area of 3 mm² formed on top of an insulated base, by using spin coat methods to sequentially produce films from a 1 (v/v %) water solution of γ-aminopropyltriethoxysilane, a 2 (w/v %) solution of acetylcellulose, a 5 (v/v %) solution of perfluorocarbonsulfonic acid resin, and then an albumin solution containing glucose oxidase and 0.5 (v/v %) of glutaraldehyde.

Evaluation of the glucose sensor was conducted by measuring the glucose concentrations in 100 (mg/dl) glucose solutions containing respectively 40 (mg/dl) of ascorbic acid, 2 (mg/dl) of uric acid, and 2 mM ortho-acetaminophen as interferents, and then comparing the measurements. Table 7 shows the output values for each of the different solutions expressed as a relative percentage value, with the measured value obtained for a 100 (mg/dl) glucose solution containing no interferents deemed to be 100%. Hence, the closer the relative percentage listed in Table 7 is to 100%, the lower the effect of that interferent on the sensor. As the results show, biosensors generated using the materials described above, with the configurations outlined above, display strong permeation restriction properties with respect to ascorbic acid, urate and acetaminophen.

TABLE 7

(Evaluation of the effect of various interferents on the measurement of glucose solutions)

| Interferent | Relative output value (%) |
| --- | --- |
| Ascorbic acid | 100 |
| Uric acid | 100 |
| ortho-acetaminophen | 102 |

EXAMPLE 8

A first glucose sensor was formed on top of a hydrogen peroxide electrode having an electrode surface area of 3 mm² formed on top of an insulated base, by using spin coat methods to sequentially produce films from a 1 (v/v %) water solution of γ-aminopropyltriethoxysilane, a 2 (w/v %) solution of acetylcellulose, a 5 (v/v %) solution of perfluorocarbonsulfonic acid resin, and then from an albumin solution containing glucose oxidase and 0.5 (v/v %) of glutaraldehyde. A second glucose sensor was formed on another hydrogen peroxide electrode of the same surface area, by using spin coat methods to sequentially produce films from a 1 (v/v %) water solution of γ-aminopropyltriethoxysilane, a 5 (v/v %) solution of perfluorocarbonsulfonic acid resin, a 2 (w/v %) solution of acetylcellulose, and then from an albumin solution containing glucose oxidase and 0.5 (v/v %) of glutaraldehyde.

Evaluation of the glucose sensors was conducted by measuring the glucose concentration in a 100 (mg/dl) glucose solution containing 40 (mg/dl) of ascorbic acid as an interferent and then comparing the measurements. Table 8 shows the output values for each of the different film configurations expressed as a relative percentage value, with the measured value obtained for a 100 (mg/dl) glucose solution containing no interferents deemed to be 100%. Hence, the closer the relative percentage listed in Table 8 is to 100%, the lower the effect is of interferents on that particular film configuration. As the results show, the glucose sensor produced by using spin coat methods to sequentially generate films from a 1 (v/v %) water solution of γ-aminopropyltriethoxysilane, a 2 (w/v %) solution of acetylcellulose, a 5 (v/v %) solution of perfluorocarbonsulfonic acid resin, and then from an albumin solution containing glucose oxidase and 0.5 (v/v %) of glutaraldehyde on top of a hydrogen peroxide electrode displayed greater permeation restriction properties with respect to the interferent.

TABLE 8

(Evaluation of the effect of interferents on glucose sensors formed with differing film configurations)

| Film configuration | Relative output value (%) |
| --- | --- |
| APTES + acetylcellulose + perfluorocarbonsulfonic acid resin | 100 |
| APTES + perfluorocarbonsulfonic acid resin + acetylcellulose | 122 |

EXAMPLE 9

Six different glucose sensors were formed on top of six separate hydrogen peroxide electrodes, each of which was formed on top of an insulated base having an electrode surface area of 3 mm², by using spin coat methods to sequentially produce films from a 1 (v/v %) water solution of γ-aminopropyltriethoxysilane, a 2 (w/v %) solution of acetylcellulose, and a 5 (v/v %) solution of perfluorocarbonsulfonic acid resin on each of the electrodes, and then following the formation of the γ-aminopropyltriethoxysilane film, the acetylcellulose film, and the perfluorocarbonsulfonic acid resin film, albumin solutions containing glucose oxidase and 0.1, 0.3, 0.5, 1.0, 1.5, 2.0 (v/v %) of glutaraldehyde respectively were dripped onto the perfluorocarbonsulfonic acid resin film of each sensor and spin coat methods used to produce an organic macromolecular film. These glucose sensors were then each used to conduct eleven repetitive measurements on a 100 (mg/dl) glucose solution. The various glutaraldehyde concentrations within the albumin solutions, and the coefficient of variation on the current output value of each glucose sensor with respect to the glucose in solution are shown in FIG. 8. As the results show, the glucose sensors which contain organic macromolecular films produced by dripping albumin solutions containing glutaraldehyde concentrations of 0.5~1.0 (v/v %), display the most stable output.

EXAMPLE 10

Figure 9:
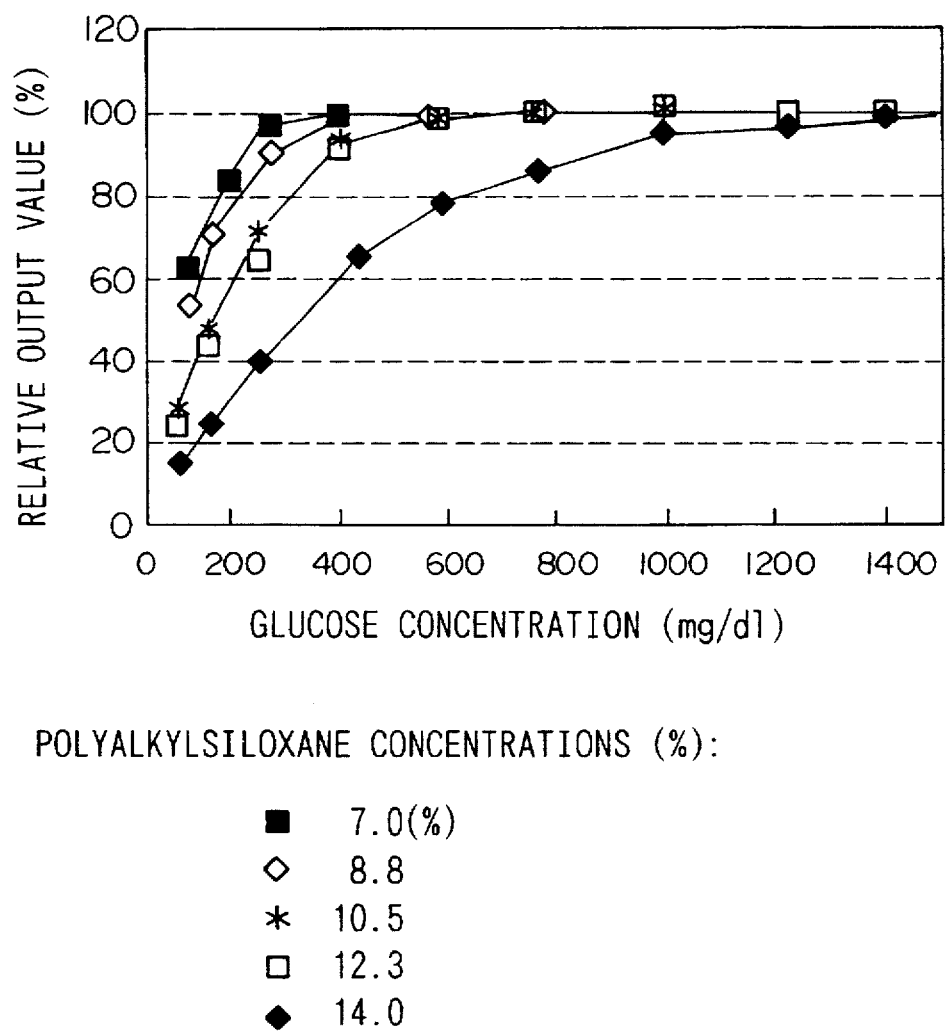
FIG. 9 is a graph showing response characteristics of glucose sensors from an example of the present invention.

A number of glucose sensors were formed on top of separate hydrogen peroxide electrodes, each of which was formed on top of an insulated base having an electrode surface area of 3 mm², by using spin coat methods to sequentially produce films from a 1 (v/v %) water solution of γ-aminopropyltriethoxysilane, a 2 (w/v %) solution of acetylcellulose, a 5 (v/v %) solution of perfluorocarbonsulfonic acid resin, and then from an albumin solution containing glucose oxidase and 0.5 (v/v %) of glutaraldehyde. A variety of polyalkylsiloxane films of differing concentrations were then formed by dripping solutions of polyalkylsiloxane of various concentrations onto the organic macromolecular films incorporating immobilized glucose oxidase, and the current output value of the various sensors measured for glucose solutions of a variety of different concentrations. The relative output values for the various sensors displayed in FIG. 9 show that restriction of the permeation of glucose is observed for polyalkylsiloxane concentrations of 7 (v/v %) or greater, and that particularly for concentrations of 10 (v/v %) or greater, the current output value does not become saturated, even with glucose concentrations of up to 500 (mg/dl), thus allowing the measurement of glucose solutions of very high concentration.

EXAMPLE 11

Figure 10:
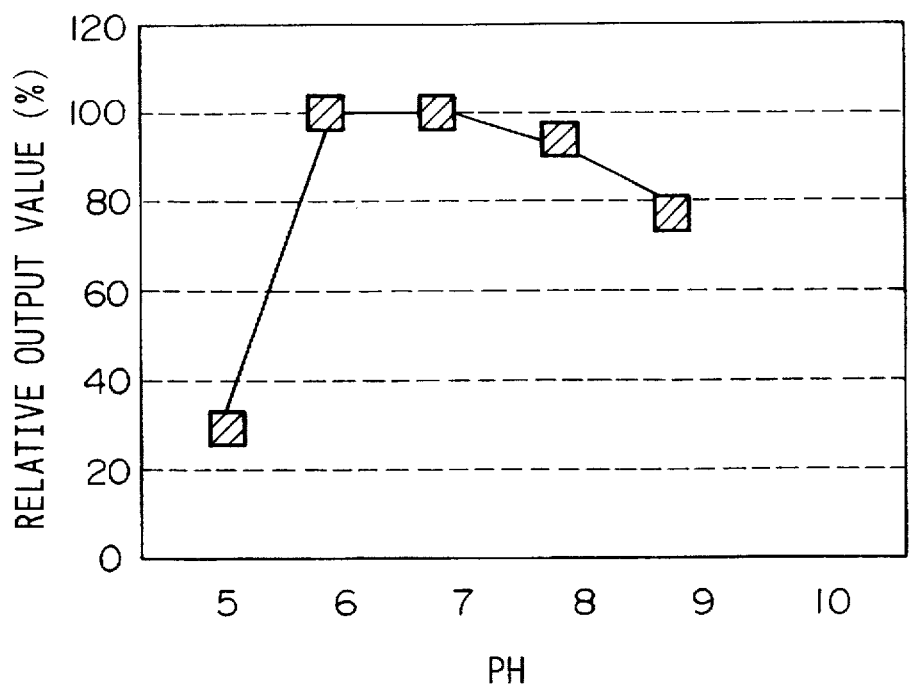
FIG. 10 is a graph showing a relationship between pH and relative output for a glucose sensor from an example of the present invention.
Figure 11:
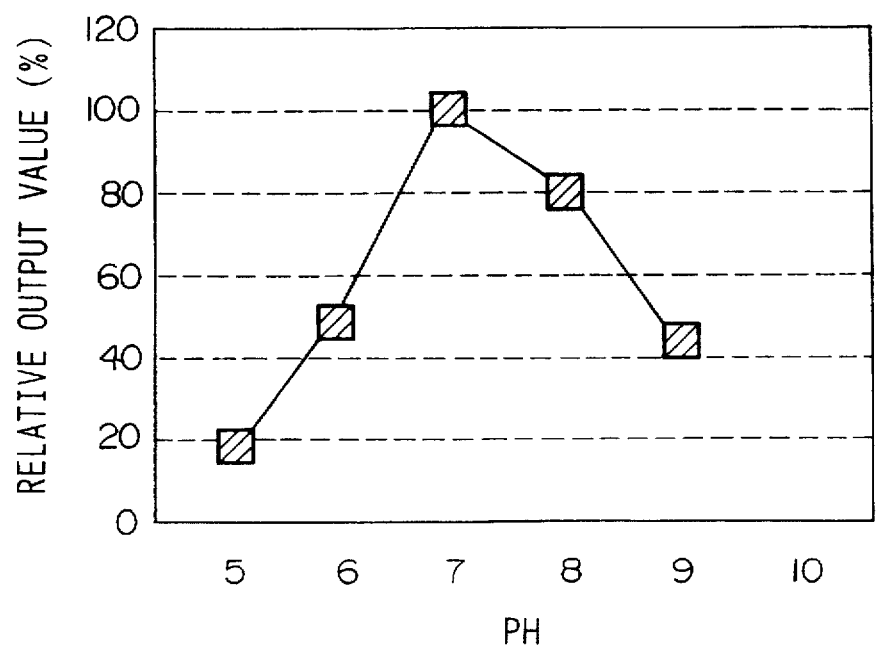
FIG. 11 is a graph showing a relationship between pH and relative output for a glucose sensor from a comparative example.
Figure 12:
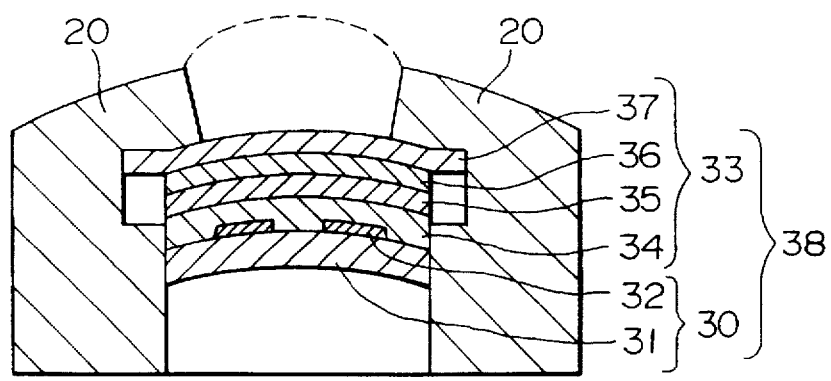
FIG. 12 is a cross-sectional diagram of an example of a biosensor based on current techniques.
Figure 13:
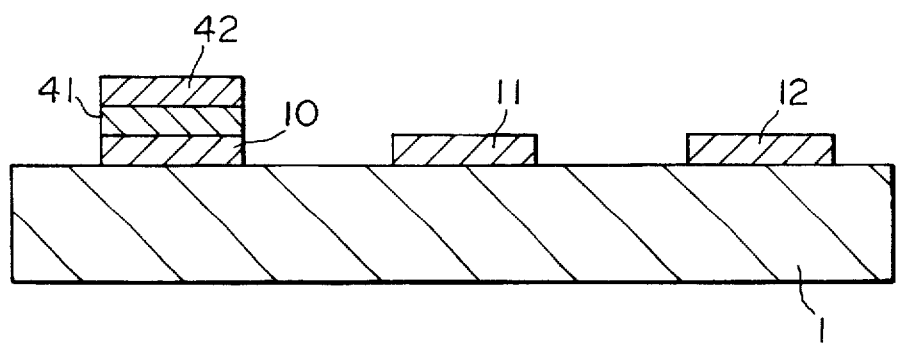
FIG. 13 is a cross-sectional diagram of another example of a biosensor based on current techniques.
Figure 14:
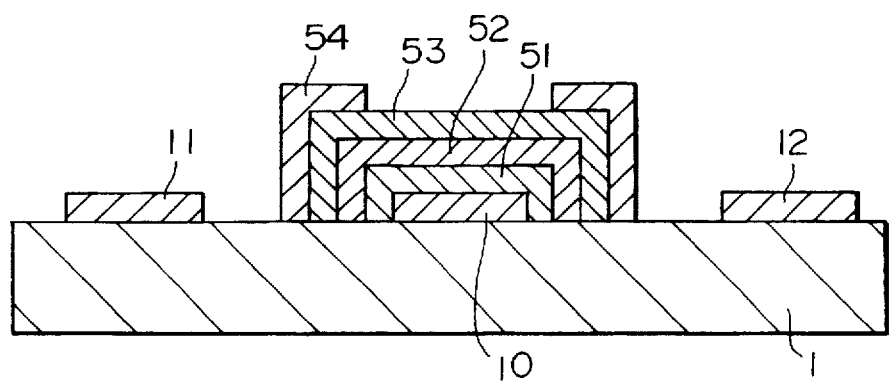
FIG. 14 is a cross-sectional diagram of yet another example of a biosensor based on current techniques.

A glucose sensor was formed on top of a hydrogen peroxide electrode having an electrode surface area of 3 mm$^2$ formed on top of an insulated base, by using spin coat methods to sequentially produce films from a 1 (v/v %) water solution of γ-aminopropyltriethoxysilane, a 2 (w/v %) solution of acetylcellulose, a 5 (v/v %) solution of perfluorocarbonsulfonic acid resin, and then an albumin solution containing glucose oxidase and 0.5 (v/v %) of glutaraldehyde. A polyalkylsiloxane film was then formed using spin coating methods by dripping a 14 (v/v %) solution of polyalkylsiloxane, prepared using silicone from Dow Corning, on top of the organic macromolecular film incorporating immobilized glucose oxidase. FIG. 10 shows the current output values for a thus formed glucose sensor, incorporating a polyalkylsiloxane film, in a variety of 100 (mg/dl) glucose solutions of differing pH, with the outputs expressed as relative percentage values, and with the measured value obtained for a glucose solution at pH 7 deemed to be 100%. FIG. 11 shows the current output values for a glucose sensor with no polyalkylsiloxane film in the same 100 (mg/dl) glucose solutions of differing pH, with the outputs expressed as relative percentage values, and with the measured value obtained for a glucose solution at pH 7 deemed to be 100%. Whereas the glucose sensor incorporating the film of polyalkylsiloxane produced output values of almost the same level within a pH range of 6~8, the output values from the sensor without the film of polyalkylsiloxane varied considerably.

What is claimed is:

1. A biosensor comprising:

an insulated base;

a hydrogen peroxide electrode formed on the insulated base, a first film which is formed on the hydrogen peroxide electrode and in which the major constituent is γ-aminopropyltriethoxysilane;

a second film which is formed on the first film and in which the major constituent is a cellulose derivative;

a third film which is formed on the second film and in which the major constituent is an ion exchange resin having a perfluorocarbon skeleton; and a fourth film which is formed on the third film and in which the major constituent is an organic macromolecular film incorporating an immobilized enzyme with catalytic properties for producing hydrogen peroxide.

2. A biosensor according to claim 1, further comprising a fifth film which is formed on the fourth film and in which the major constituent is polyalkylsiloxane.

3. A biosensor according to claim 1, wherein the concentration of γ-aminopropyltriethoxysilane at the time of forming the film is within a range of 0.5~2 (v/v %).

4. A biosensor according to claim 1, wherein the cellulose derivative is acetylcellulose, and the concentration of this acetylcellulose at the time of forming the film is within a range of 0.5~5 (w/v %).

5. A biosensor according to claim 1, wherein the ion exchange resin based having a perfluorocarbon skeleton is perfluorocarbonsulfonic acid resin, and the concentration of this perfluorocarbonsulfonic acid resin at the time of forming the film is 1 (v/v %) or greater.

6. A biosensor according to claim 1, wherein a solution of glutaraldehyde and albumin is used at the time of forming the organic macromolecular film incorporating an immobilized enzyme with catalytic properties, and the concentration of the glutaraldehyde is within a range of 0.1~2 (v/v %).

7. A biosensor according to claim 2, wherein the concentration of polyalkylsiloxane at the time of forming the film is 7.0 (v/v %) or greater.

8. A biosensor according to claim 1, wherein the hydrogen peroxide electrode on the insulated base is made up of a working electrode, a counter electrode, and a reference electrode.

9. A biosensor according to claim 8, wherein two or more working electrodes are formed on the insulated base, and at the same time two or more types of organic macromolecular films incorporating an immobilized enzyme with catalytic properties are formed.

* * * * *